United States Patent
Nakazato et al.

(10) Patent No.: US 7,557,111 B2
(45) Date of Patent: Jul. 7, 2009

(54) SUBSTITUTED THIENO[3,2-D]PYRIMIDINES AS CRF RECEPTOR ANTAGONISTS

(75) Inventors: Atsuro Nakazato, Tokyo (JP); Taketoshi Okubo, Tokyo (JP); Dai Nozawa, Tokyo (JP); Tomoko Tamita, Tokyo (JP); Ludo E. J. Kennis, Beerse (BE)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 176 days.

(21) Appl. No.: 10/584,951

(22) PCT Filed: Jan. 6, 2005

(86) PCT No.: PCT/JP2005/000318

§ 371 (c)(1), (2), (4) Date: Sep. 13, 2006

(87) PCT Pub. No.: WO2005/066182

PCT Pub. Date: Jul. 21, 2005

(65) Prior Publication Data

US 2007/0254898 A1    Nov. 1, 2007

(30) Foreign Application Priority Data

Jan. 6, 2004   (JP) ................ 2004-001310

(51) Int. Cl.
C07D 495/04 (2006.01)
A61K 31/519 (2006.01)

(52) U.S. Cl. .................. 514/260.1; 544/278

(58) Field of Classification Search .......... 544/114; 514/301
See application file for complete search history.

(56) References Cited

U.S. PATENT DOCUMENTS

| | | | |
|---|---|---|---|
| 6,187,781 B1 | 2/2001 | Nakazato et al. | |
| 6,600,038 B1 | 7/2003 | Nakazato et al. | |
| 6,852,732 B2 * | 2/2005 | Nakazato et al. | 514/307 |
| 2005/0209253 A1 | 9/2005 | Nakazato et al. | |
| 2007/0060602 A1 | 3/2007 | Nakazato et al. | |
| 2007/0254898 A1 | 11/2007 | Nakazato et al. | |

FOREIGN PATENT DOCUMENTS

| | | |
|---|---|---|
| EP | 0729758 A2 | 9/1996 |
| WO | 94/13676 A1 | 6/1994 |
| WO | WO 97/29110 A1 | 8/1997 |
| WO | WO 98/42699 A1 | 1/1998 |
| WO | 98/08847 A1 | 3/1998 |
| WO | 98/35967 A2 | 8/1998 |
| WO | WO 98/47903 A1 | 10/1998 |
| WO | 99/51597 A1 | 10/1999 |
| WO | 99/51599 A1 | 10/1999 |
| WO | 99/51600 A1 | 10/1999 |
| WO | WO 00/53604 A1 | 9/2000 |
| WO | WO 02/02549 A1 | 1/2002 |
| WO | WO 2004/058767 A1 | 7/2004 |
| WO | WO 2005/066142 A3 | 7/2005 |
| WO | WO 2005/066178 A1 | 7/2005 |
| WO | WO 2005/066182 A1 | 7/2005 |
| WO | WO 2005/085253 A1 | 9/2005 |
| WO | WO 2006/001501 A1 | 1/2006 |
| WO | WO 2006/001511 A1 | 1/2006 |

OTHER PUBLICATIONS

Vippagunta et. al. (Advanced Drug Delivery Review, 2001, 48, 3-26.*

Mario Bonamico et al., "Condensation Reactions of Tetracyanoethylene and its Monoanion Promoted by Lewis Acids: Synthesis and Crystal, Moleuclar, and Electronic Structure of a Novel Heterocycle, the 2, 3, 6, 7-Tetracyano-5-(tricyanoethenylimino)-3H-1,4,7b-triazabenzo[i,j]pentalenide Ion", J. Chem. Soc. Perkin Trans. 2, 121-125 (1990).

* cited by examiner

*Primary Examiner*—Brenda L Coleman
*Assistant Examiner*—Susanna Moore
(74) *Attorney, Agent, or Firm*—Sughrue Mion, PLLC

(57) ABSTRACT

An object of the present invention is to provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, epilepsy, dermatitides, schizophrenia, etc.

A thienopyrimidine or thienopyridine derivative substituted with a cyclic amino group represented by the following formula [I]:

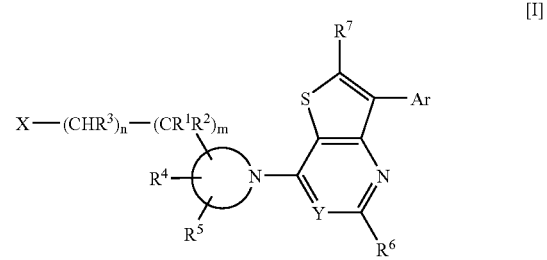

has a high affinity for CRF receptors and is effective against diseases in which CRF is considered to be involved.

7 Claims, No Drawings

SUBSTITUTED THIENO[3,2-D]PYRIMIDINES AS CRF RECEPTOR ANTAGONISTS

This Application is a 371 of PCT/JP2005/000318, filed Jan. 6, 2005; the disclosure of which is incorporated herein by reference.

DETAILED DESCRIPTION OF THE INVENTION

1. Technical Field

The present invention relates to a therapeutic agent for diseases in which corticotropin releasing factor (CRF) is considered to be involved, such as depression, anxiety, Alzheimer's disease, Parkinson's disease, Huntington's chorea, eating disorder, hypertension, gastral diseases, drug dependence, cerebral infarction, cerebral ischemia, cerebral edema, cephalic external wound, inflammation, immunity-related diseases, alpecia, irritable bowel syndrome, sleep disorders, epilepsy, dermatitides, schizophrenia, pain, etc.

2. Description of the Prior Art

CRF is a hormone comprising 41 amino acids (Science, 213, 1394-1397, 1981; and J. Neurosci., 7, 88-100, 1987), and it is suggested that CRF plays a core role in biological reactions against stresses (Cell. Mol. Neurobiol., 14, 579-588, 1994; Endocrinol., 132, 723-728, 1994; and Neuroendocrinol. 61, 445-452, 1995). For CRF, there are the following two paths: a path by which CRF acts on peripheral immune system or sympathetic nervous system through hypothalamus-pituitary-adrenal system, and a path by which CRF functions as a neurotransmitter in central nervous system (in Corticotropin Releasing Factor: Basic and Clinical Studies of a Neuropeptide, pp. 29-52, 1990). Intraventricular administration of CRF to hypophysectomized rats and normal rats causes an anxiety-like symptom in both types of rats (Pharmacol. Rev., 43, 425-473, 1991; and Brain Res. Rev., 15, 71-100, 1990). That is, there are suggested the participation of CRF in hypothalamus-pituitary-adrenal system and the pathway by which CRF functions as a neurotransmitter in central nervous system.

The review by Owens and Nemeroff in 1991 summarizes diseases in which CRF is involved (Pharmacol. Rev., 43, 425-474, 1991). That is, CRF is involved in depression, anxiety, Alzheimer's disease, Parkinson's disease, Huntington's chorea, eating disorder, hypertension, gastrointestinal diseases, drug dependence, inflammation, immunity-related diseases, etc. It has recently been reported that CRF is involved also in epilepsy, cerebral infarction, cerebral ischemia, cerebral edema, and cephalic external wound (Brain Res. 545, 339-342, 1991; Ann. Neurol. 31, 48-498, 1992; Dev. Brain Res. 91, 245-251, 1996; and Brain Res. 744, 166-170, 1997). Accordingly, antagonists against CRF receptors are useful as therapeutic agents for the diseases described above.

WO02/002549, WO97/29110 and WO98/47903 disclose thienopyridine and thienopyrimidine derivatives respectively as CRF receptor antagonists. However, none disclose the compounds provided in the present invention.

PROBLEM(S) TO BE SOLVED BY INVENTION

An object of the present invention is to provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, dermatitides, schizophrenia, pain, etc.

MEANS FOR SOLVING PROBLEM

The present inventors earnestly investigated thienopyrimidine or thienopyridine derivatives substituted with a cyclic amino group that have a high affinity for CRF receptors, whereby the present invention has been accomplished.

The present invention is thienopyrimidine or thienopyridine derivatives substituted with a cyclic amino group explained below.

A thienopyrimidine or thienopyridine derivative substituted with a cyclic amino group represented by the following formula [I]:

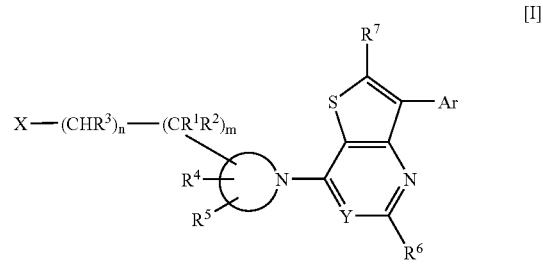

(wherein the cyclic amino group is represented by the following formula [II]:

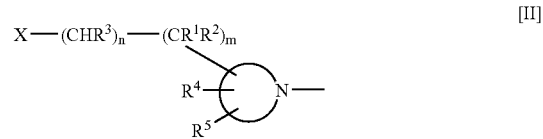

in which the cyclic amino group is a 3- to 8-membered saturated cyclic amine or a 3- to 8-membered saturated cyclic amine bridged with $C_{1-5}$alkylene or $C_{1-4}$alkylene-O-$C_{1-4}$alkylene between any different two carbon atoms of the cyclic amine, which cyclic amine is substituted with a group represented by —$(CR^1R^2)_m$—$(CHR^3)_n$—X, $R^4$ and $R^5$ independently on the same or different carbon atoms of the cyclic amine;

X is cyano, hydroxy, —$CO_2R^8$ or —$CONR^9R^{10}$;

Y is N or $CR^{11}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, halogen, $C_{1-5}$alkylthio or —$N(R^{12})R^{13}$;

$R^7$ is hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —$N(R^{14})R^{15}$, —$CO_2R^{16}$, —$CON(R^{17})R^{18}$, cyano, nitro, $C_{1-5}$alkylthio, trifluoromethyl or trifluoromethoxy;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{19}$, —$C(=O)R^{20}$, —$CONR^{21}R^{22}$, —$OC(=O)R^{23}$, $NR^{24}CO_2R^{25}$, —$S(=O)_r$ $NR^{26}R^{27}$, trifluoromethyl, trifluoromethoxy, difluoromethoxy, fluoromethoxy, methylenedioxy, ethylenedioxy and —$N(R^{28})R^{29}$;

$R^8$ is hydrogen, $C_{1-10}$alkyl, $C_{3-8}$cycloalkyl, $C_{3-8}$cycloalkyl-$C_{1-5}$alkyl, aryl or aryl-$C_{1-5}$alkyl;

$R^9$ and $R^{10}$ are the same or different, and independently are hydrogen, $C_{1-5}$alkyl, $C_{3-8}$cycloalkyl, $C_{3-8}$cycloalkyl-$C_{1-5}$alkyl, aryl or aryl-$C_{1-5}$alkyl; or $R^9$ and $R^{10}$ form a ring selected from saturated 3 to 8 membered ring with the attached nitrogen atom, wherein one of the carbon atoms of such saturated 3 to 8 membered ring is optionally replaced by an oxygen or sulfur atom or by N-Z wherein Z is hydrogen, benzyl or $C_{1-5}$alkyl;

$R^{11}$ is hydrogen, halogen or $C_{1-5}$alkyl;

$R^{12}$, $R^{13}$, $R^{14}$ and $R^{15}$ are the same or different, and independently are hydrogen or $C_{1-5}$alkyl;

$R^{16}$, $R^{19}$ and $R^{25}$ are the same or different, and independently are hydrogen or $C_{1-5}$alkyl, $C_{3-8}$cycloalkyl, $C_{3-8}$cycloalkyl-$C_{1-5}$alkyl, aryl or aryl-$C_{1-5}$alkyl;

$R^{17}$, $R^{18}$, $R^{20}$, $R^{21}$, $R^{22}$, $R^{23}$, $R^{24}$, $R^{26}$, $R^{27}$, $R^{28}$ and $R^{29}$ are the same or different, and independently are hydrogen, $C_{1-5}$alkyl or $C_{3-8}$cycloalkyl;

r is 1 or 2), individual isomers thereof or racemic or non-racemic mixtures of isomers thereof, pharmaceutically acceptable prodrugs thereof or pharmaceutically acceptable salts and hydrates thereof.

The terms used in the present specification have the following meanings.

The term "a 3- to 8-membered saturated cyclic amine" means aziridine, azetidine, pyrrolidine, piperidine, azepane or azocane.

The term "$C_{1-5}$alkylene" means a straight or branched chain alkylene of 1 to 5 carbon atoms, such as methylene, ethylene, propylene, trimethylene, tetramethylene, pentamethylene or the like.

The term "a 3- to 8-membered saturated cyclic amine bridged with $C_{1-5}$alkylene or $C_{1-4}$alkylene-O—$C_{1-4}$alkylene between any different two carbon atoms of the cyclic amine" includes, for example, 8-azabicyclo[3.2.1]oct-8-yl, 9-azabicyclo[3.3.1]non-9-yl, 7-azabicyclo[2.2.1]hept-7-yl, 3-oxa-7-azabicyclo[3.3.1]non-7-yl and 3-oxa-9-azabicyclo[3.3.1]non-9-yl.

The term "$C_{1-5}$alkyl" means a straight chain or branched chain alkyl group of 1 to 5 carbon atoms, such as methyl, ethyl, propyl, isopropyl, butyl, isobutyl, t-butyl, sec-butyl, pentyl, isopentyl or the like.

The term "$C_{1-5}$alkoxy" means a straight chain or branched chain alkoxy group of 1 to 5 carbon atoms, such as methoxy, ethoxy, propoxy, isopropyloxy, butoxy, isobutyloxy, pentyloxy, isopentyloxy or the like.

The term "$C_{1-5}$alkoxy-$C_{1-5}$alkyl" means a substituted $C_{1-5}$alkyl group having the above-mentioned $C_{1-5}$alkoxy group as the substituent, such as methoxymethyl, 2-methoxyethyl, 2-ethoxyethyl or the like.

The term "hydroxy-$C_{1-5}$alkyl" means a substituted $C_{1-5}$alkyl group having hydroxy group, such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl or the like.

The term "cyano-$C_{1-5}$alkyl" means a substituted $C_{1-5}$alkyl group having cyano group, such as cyanomethyl, 1-cyanoethyl, 2-cyanoethyl, 3-cyanopropyl, 4-cyanobutyl, 5-cyanopentyl or the like.

The term "$C_{3-8}$cycloalkyl" means a cyclic alkyl group of 3 to 8 carbon atoms, such as cyclopropyl, cyclobutyl, cyclopentyl, cyclohexyl, cycloheptyl or the like.

The term "$C_{3-8}$cycloalkyl-$C_{1-5}$alkyl" means a substituted $C_{1-5}$alkyl group having the above-mentioned $C_{3-8}$cycloalkyl as the substituent, such as cyclopropylmethyl, 2-cyclopropylethyl, 2-cyclopentylethyl or the like.

The term "$C_{3-8}$cycloalkyloxy" means a cyclic alkoxy group of 3 to 8 carbon atoms, such as cyclopropyloxy, cyclobutyloxy, cyclopentyloxy or the like.

The term "halogen" means fluorine, chlorine, bromine or iodine atom.

The term "$C_{1-5}$alkylthio" means a straight chain or branched chain alkylthio group of 1 to 5 carbon atoms, such as methylthio, ethylthio, propylthio or the like.

The term "$C_{1-5}$alkylsulfinyl" means a straight chain or branched chain alkylsulfinyl group of 1 to 5 carbon atoms, such as methylsulfinyl, ethylsulfinyl, propylsulfinyl or the like.

The term "$C_{1-5}$alkylsulfonyl" means a straight chain or branched chain alkylsulfonyl group of 1 to 5 carbon atoms, such as methylsulfonyl, ethylsulfonyl, propylsulfonyl or the like.

The term "aryl" means a monocyclic or bicyclic group of 6 to 12 ring carbon atoms having at least one aromatic ring, such as phenyl, naphthyl, or the like.

The term "heteroaryl" means a monocyclic or bicyclic group of 5 to 12 ring atoms having at least one aromatic ring having in its ring 1 to 4 atoms which may be the same or different and are selected from nitrogen, oxygen and sulfur, such as pyridyl, pyrimidinyl, imidazolyl, quinolyl, indolyl, benzofuranyl, quinoxalinyl, benzo[1,2,5]thiadiazolyl, benzo [1,2,5]oxadiazolyl or the like.

The term "ary-$C_{1-5}$alkyl" means a substituted $C_{1-5}$alkyl group having the above-mentioned aryl as the substituent, such as benzyl, phenethyl or the like.

The term "$C_{2-5}$alkenyl" means a straight chain or branched chain alkenyl group of 2 to 5 carbon atoms, such as vinyl, isopropenyl, alkyl or the like.

The term "$C_{2-5}$alkynyl" means a straight chain or branched chain alkynyl group of 2 to 5 carbon atoms, such as ethynyl, prop-1-ynyl, prop-2-ynyl or the like.

The phrase "aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{19}$, —$C(=O)R^{20}$, —$CONR^{21}R^{22}$, —$OC(=O)R^{23}$, —$NR^{24}CO_2R^{25}$, —$S(=O)_rNR^{26}R^{27}$, trifluoromethyl, trifluoromethoxy, difluoromethoxy, fluoromethoxy, methylenedioxy, ethylenedioxy and —$N(R^{28})R^{29}$" includes, for example, 2,4-dimethylphenyl, 2,6-dimethylphenyl, 2,4-dibromophenyl, 2-bromo-4-isoproylphenyl, 2,4-dichlorophenyl, 2,6-dichlorophenyl, 2-chloro-4-trifluoromethylphenyl, 4-methoxy-2-methylphenyl, 2-chloro-4-trifluoromethoxyphenyl, 4-isopropyl-2-methylthiophenyl, 2,4,6-trimethylphenyl, 4-bromo-2,6-dimethylphenyl, 4-bromo-2,6-diethylphenyl, 4-chloro-2,6-dimethylphenyl, 2,4,6-tribromophenyl, 2,4,5-tribromophenyl, 2,4,6-trichlorophenyl, 2,4,5-trichlorophenyl, 4-bromo-2,6-dichlorophenyl, 6-chloro-2,4-dibromophenyl, 2,4-dibromo-6-fluorophenyl, 2,4-dibromo-6-methylphenyl, 2,4-dibromo-6-methoxyphenyl, 2,4-dibromo-6-methylthiophenyl, 2,6-dibromo-4-isopropylphenyl, 2,6-dibromo-4-trifluoromethylphenyl, 2-bromo-4-trifluoromethylphenyl, 4-bromo-2-chlorophenyl, 2-bromo-4-chlorophenyl, 4-bromo-2-methylphenyl, 4-chloro-2-methylphenyl, 2,4-dimethoxyphenyl, 2,6-dimethyl-4-methoxyphenyl, 4-chloro-2,6-dibromophenyl, 4-bromo-2,6-difluorophenyl, 2,6-dichloro-4-trifluoromethylphenyl, 2,6-dichloro-4-trifluoromethoxyphenyl, 2,6-dibromo-4-trifluoromethoxyphenyl, 2-chloro-4,6-dimethylphenyl, 2-bromo-4,6-dimethoxyphenyl, 2-bromo-4-isopropyl-6-methoxyphenyl, 2,4-dimethoxy-6-methylphenyl, 6-dimethylamino-4-methylpyridin-3-yl, 2-chloro-6-trifluoromethylpyridin-3-yl, 2-chloro-6-trifluoromethoxypyridin-3-yl, 2-chloro-6-methoxypyridin-3-yl, 6-methoxy-2-trifluoromethylpyridin-3-yl, 2-chloro-6-difluoromethylpyridin-3-yl, 6-methoxy-2-methylpyridin-3-yl, 2,6-dimethoxypyridin-3-yl, 4,6-dimethyl-2-trifluoromethylpyrimidin-5-yl or 2-dimethylamino-6-methylpyridin-3-yl.

The "pharmaceutically acceptable salts" in the present invention include, for example, salts with an inorganic acid such as sulfuric acid, hydrochloric acid, hydrobromic acid, phosphoric acid, nitric acid or the like; salts with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like; salts with one or more metal ions such as lithium ion, sodium ion, potassium ion, calcium ion, magnesium ion, zinc ion, aluminium ion or the like; salts with amines such as ammonia, arginine, lysine, piperazine, choline, diethylamine, 4-phenylcyclohexylamine, 2-aminoethanol, benzathine or the like.

Prodrugs are also included in this invention. The term "prodrug" means a compound which is converted within the body, e.g. by hydrolysis in the blood, into its active form that has medical effects. The "pharmaceutically acceptable prodrugs" are described in, for example, Advanced Drug Delivery Reviews (1996) 19 (2) 115-130 and Tetrahedron Letter (2002) 43 1161-1164. The "pharmaceutically acceptable prodrugs thereof" in the present invention include, for example, esters such as methyl esters, ethyl esters, and the like when X is carboxylic acid.

A compound of the present invention includes any isomers such as diastereomers, enantiomers, geometricisomers and tautomeric forms. In a compound represented by formula [I], if the cyclic amino group has one or more chiral carbons and/or if there is an axial chirality between Ar and thienopyrimidine (or thienopyridine) ring, several stereoisomers (diastereomers or enantiomers) can exist. The compound of the present invention includes the individual isomers and the racemic and non-racemic mixtures of the isomers.

Preferable examples of the compound of the present invention are as follows.

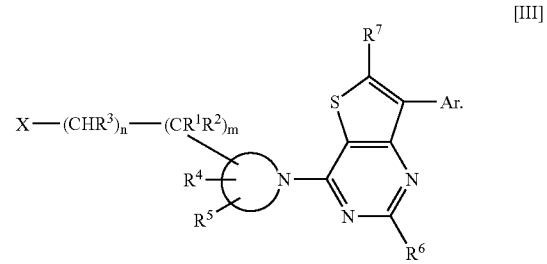

[III]

That is preferable are compounds of the formula [III] in which X, m, n, the cyclic amino group, $R^1$, $R^2$, $R^3$, $R^4$, $R^5$, $R^6$, $R^7$ and Ar are as defined in above formula [I]. More preferable are compounds of the formula [III] in which X is cyano; the cyclic amino group is a 4- to 7-membered saturated cyclic amine; n is 0; m is 0, 1, 2 and 3; $R^1$, $R^2$, $R^4$ and $R^5$ are hydrogen; $R^6$ is $C_{1-5}$alkyl; $R^7$ is hydrogen or $C_{1-5}$alkyl; and Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N($R^{28}$)$R^{29}$ (wherein $R^{28}$ and $R^{29}$ are the same or different, and independently are hydrogen or $C_{1-3}$alkyl). More preferable are compounds of the formula [III] in which X is cyano; the cyclic amino group is a 6-membered saturated cyclic amine; n is 0; m is 0 or 1; $R^1$, $R^2$, $R^4$ and $R^5$ are hydrogen; $R^6$ is $C_{1-5}$alkyl; $R^7$ is hydrogen or $C_{1-5}$alkyl; and Ar is phenyl which phenyl is substituted with two or three substituents, which are the same or different, selected from the group consisting of halogen and $C_{1-3}$alkyl.

Other preferable are compounds of the formula [III] in which X is hydroxy; the cyclic amino group is a 4- to 7-membered saturated cyclic amine; n is 0; m is an integer selected from 1, 2 and 3; $R^1$, $R^2$, $R^4$ and $R^5$ are hydrogen; $R^6$ is $C_{1-5}$alkyl; $R^7$ is hydrogen or $C_{1-5}$alkyl; and Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N($R^{28}$)$R^{29}$ (wherein $R^{28}$ and $R^{29}$ are the same or different, and independently are hydrogen or $C_{1-3}$alkyl). More preferable are compounds of the formula [III] in which X is hydroxy; the cyclic amino group is a 6-membered saturated cyclic amine; n is 0; m is an integer selected from 1, 2 and 3; $R^1$, $R^2$, $R^4$ and $R^5$ are hydrogen; $R^6$ is $C_{1-5}$alkyl; $R^7$ is hydrogen or $C_{1-5}$alkyl; and Ar is phenyl which phenyl is substituted with two or three substituents, which are the same or different, selected from the group consisting of halogen and $C_{1-3}$alkyl.

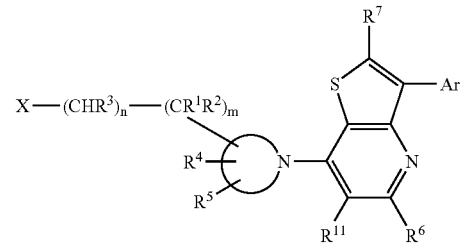

[IV]

Other preferable are compounds of the formula [IV] in which X, m, n, the cyclic amino group, R¹, R², R³, R⁴, R⁵, R⁶, R⁷, R¹¹ and Ar are as defined in above formula [I]. More preferable are compounds of the formula [IV] in which X is cyano; the cyclic amino group is a 4- to 7-membered saturated cyclic amine; n is 0; m is 0 or 1; R¹, R², R⁴ and R⁵ are hydrogen; R⁶ is $C_{1-5}$alkyl; R⁷ is hydrogen or $C_{1-5}$alkyl; R¹¹ is hydrogen or $C_{1-5}$alkyl; and Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N(R²⁸)R²⁹ (wherein R²⁸ and R²⁹ are the same or different, and independently are hydrogen or $C_{1-3}$alkyl). More preferable are compounds of the formula [IV] in which X is cyano; the cyclic amino group is a 6-membered saturated cyclic amine; n is 0; m is 0 or 1; R¹, R², R⁴ and R⁵ are hydrogen; R⁶ is $C_{1-5}$alkyl; R⁷ is hydrogen or $C_{1-5}$alkyl; R¹¹ is hydrogen; and Ar is phenyl which phenyl is substituted with two or three substituents, which are the same or different, selected from the group consisting of halogen and $C_{1-3}$alkyl.

Other preferable are compounds of the formula [IV] in which X is hydroxy; the cyclic amino group is a 4- to 7-membered saturated cyclic amine; n is 0; m is an integer selected from 1, 2 and 3; R¹, R², R⁴ and R⁵ are hydrogen; R⁶ is $C_{1-5}$alkyl; R⁷ is hydrogen or $C_{1-5}$alkyl; R¹¹ is hydrogen or $C_{1-5}$alkyl; and Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N(R²⁸)R²⁹ (wherein R²⁸ and R²⁹ are the same or different, and independently are hydrogen or $C_{1-3}$alkyl). More preferable are compounds of the formula [IV] in which X is hydroxy; the cyclic amino group is a 6-membered saturated cyclic amine; n is 0; m is an integer selected from 1, 2 and 3; R¹, R², R⁴ and R⁵ are hydrogen; R⁶ is $C_{1-5}$alkyl; R⁷ is hydrogen or $C_{1-5}$alkyl; R¹¹ is hydrogen; and Ar is phenyl which phenyl is substituted with two or three substituents, which are the same or different, selected from the group consisting of halogen and $C_{1-3}$alkyl.

The preferable cyclic amino group is a 6-membered saturated cyclic amine.

The preferable R¹ is hydrogen.

The preferable R² is hydrogen.

The preferable R³ is hydrogen.

The preferable R⁴ is hydrogen.

The preferable R⁵ is hydrogen.

The preferable R⁶ is $C_{1-3}$alkyl. The more preferable R⁶ is methyl.

The preferable R⁷ is hydrogen or $C_{1-3}$alkyl.

The preferable R¹¹ is hydrogen.

The preferable Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N(R²⁸)R²⁹ (wherein R²⁸ and R²⁹ are the same or different, and independently are hydrogen or $C_{1-3}$alkyl). The more preferable Ar is phenyl which phenyl is substituted with two or three substituents, which are the same or different, selected from the group consisting of halogen, $C_{1-3}$alkyl, and $C_{1-3}$alkoxy.

Especially preferable compounds of the present invention are:

{1-[7-(4-bromo-2,6-dimethyl-phenyl)-2-methyl-thieno[3,2-d]pyrimidin-4-yl]-piperidin-4-yl}-methanol

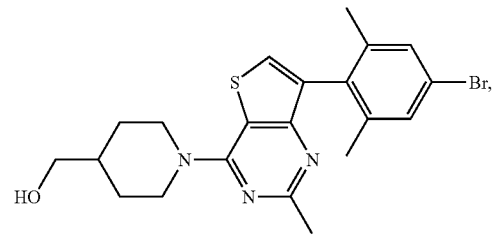

{1-[7-(4-bromo-2,6-dimethyl-phenyl)-2,6-dimethyl-thieno[3,2-d]pyrimidin-4-yl]-piperidin-4-yl}-methanol

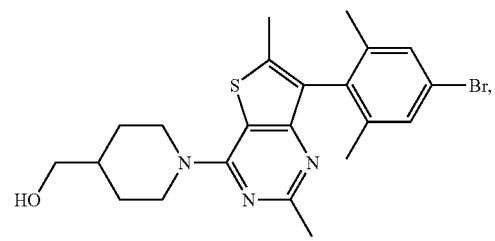

2-{1-[7-(4-bromo-2,6-dimethyl-phenyl)-2,6-dimethyl-thieno[3,2-d]pyrimidin-4-yl]-piperidin-4-yl}-ethanol

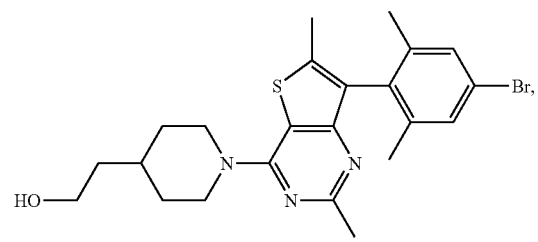

{1-[7-(4-bromo-2,6-dimethyl-phenyl)-2,6-dimethyl-thieno[3,2-d]pyrimidin-4-yl]-piperidin-4-yl}-acetonitrile

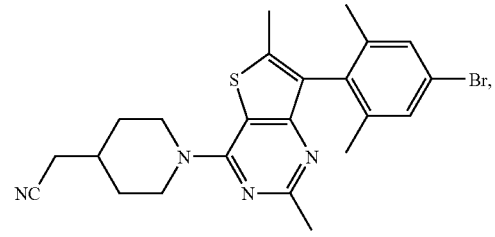

9

{1-[3-(2,4-dichloro-phenyl)-5-methyl-thieno[3,2-b]pyridin-7-yl]-piperidin-4-yl}-methanol

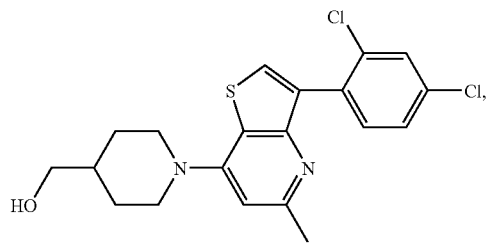

{1-[5-methyl-3-(2,4,6-trimethyl-phenyl)-thieno[3,2-b]pyridin-7-yl]-piperidin-4-yl}-methanol

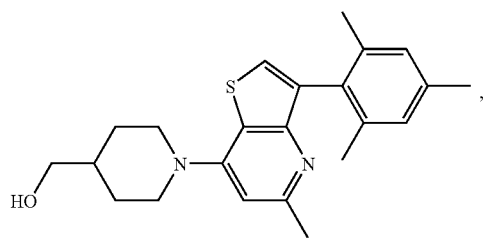

{1-[3-(4-bromo-2,6-dimethyl-phenyl)-5-methyl-thieno[3,2-b]pyridin-7-yl]-piperidin-4-yl}-methanol

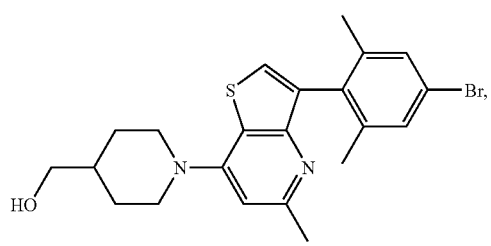

{1-[3-(4-bromo-2,6-dimethyl-phenyl)-2,5-dimethyl-thieno[3,2-b]pyridin-7-yl]-piperidin-4-yl}-methanol

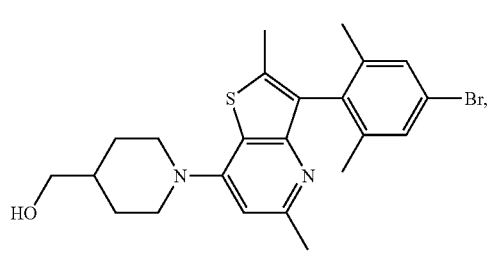

10

{1-[3-(2,4-dibromo-phenyl)-5-methyl-thieno[3,2-b]pyridin-7-yl]-piperidin-4-yl}-methanol {1-[5-methyl-3-(2,4,6-trichloro-phenyl)-thieno[3,2-b]pyridin-7-yl]-piperidin-4-yl}-methanol

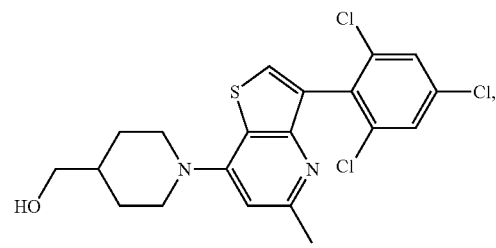

2-{1-[3-(4-bromo-2,6-dimethyl-phenyl)-5-methyl-thieno[3,2-b]pyridin-7-yl]-piperidin-4-yl}-ethanol

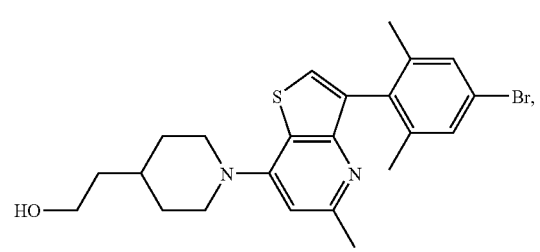

2-{1-[3-(4-bromo-2,6-dimethyl-phenyl)-2,5-dimethyl-thieno[3,2-b]pyridin-7-yl]-piperidin-4-yl}-ethanol

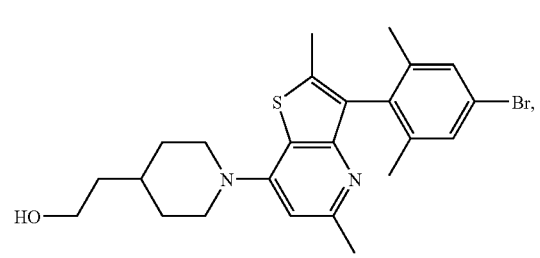

11

2-{1-[3-(2,4-dibromo-phenyl)-5-methyl-thieno[3,2-b]pyridin-7-yl]-piperidin-4-yl}-ethanol

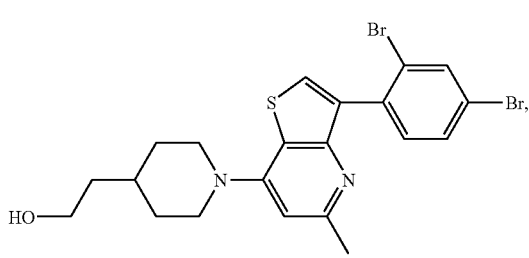

2-{1-[5-methyl-3-(2,4,6-trichloro-phenyl)-thieno[3,2-b]pyridin-7-yl]-piperidin-4-yl}-ethanol

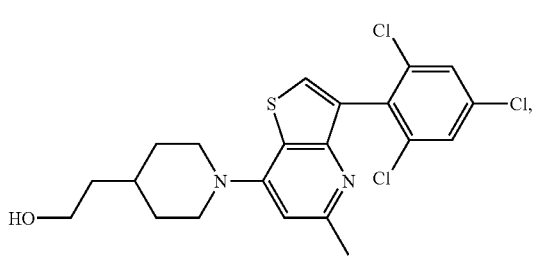

1-[5-methyl-3-(2,4,6-trimethyl-phenyl)-thieno[3,2-b]pyridin-7-yl]-piperidine-3-carbonitrile

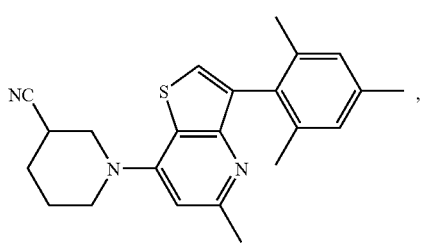

{1-[3-(4-bromo-2,6-dimethyl-phenyl)-5-methyl-thieno[3,2-b]pyridin-7-yl]-piperidin-4-yl}-acetonitrile

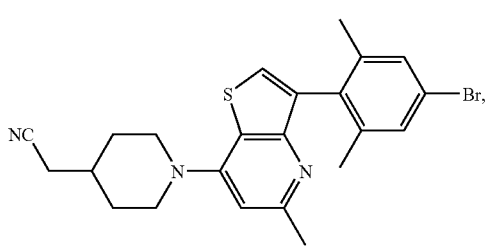

12

{1-[3-(4-bromo-2,6-dimethyl-phenyl)-2,5-dimethyl-thieno[3,2-b]pyridin-7-yl]-piperidin-4-yl}-acetonitrile

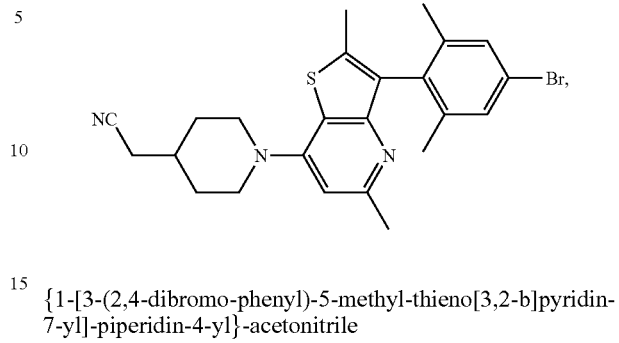

{1-[3-(2,4-dibromo-phenyl)-5-methyl-thieno[3,2-b]pyridin-7-yl]-piperidin-4-yl}-acetonitrile

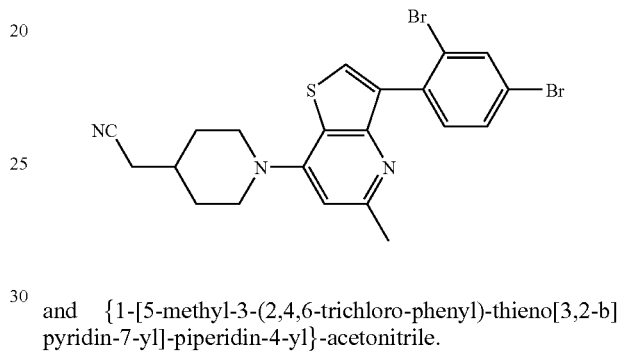

and {1-[5-methyl-3-(2,4,6-trichloro-phenyl)-thieno[3,2-b]pyridin-7-yl]-piperidin-4-yl}-acetonitrile.

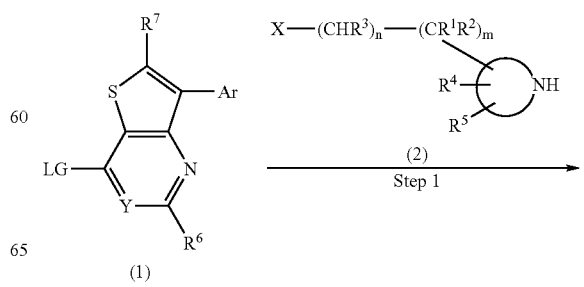

The compound of the formula [I] can be produced, for example, by the process shown in the following reaction scheme 1 (in the following reaction scheme, $R^1$, $R^2$, $R^3$, $R^4$, $R^5$, $R^6$, $R^7$, $R^9$, $R^{10}$, m, n, X, Y and Ar are as defined above, LG is chloro, bromo, iodo, methanesulfonyloxy, benzenesulfonyloxy, toluenesulfonyloxy or trifluoromethanesulfonyloxy, $X^a$ is carboxy, carbamoyl or —$CO_2(C_{1-5}alkyl)$, $X^b$ is $CO_2(C_{1-5}alkyl)$ or $CONR^9R^{10}$).

Reaction Scheme 1

Reaction Scheme 2

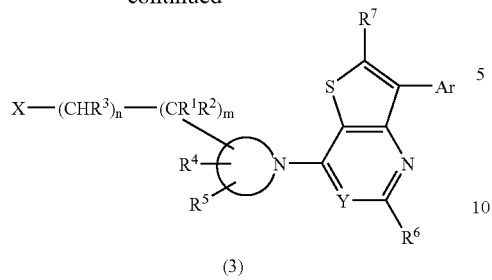

(3)

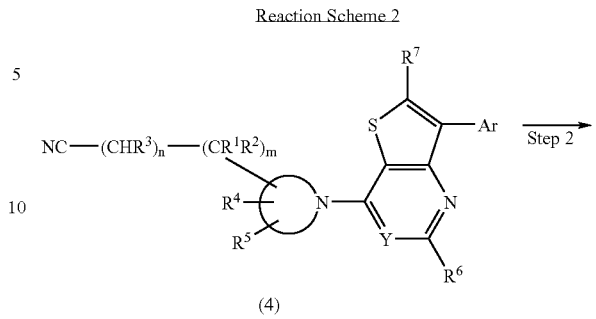

(4)

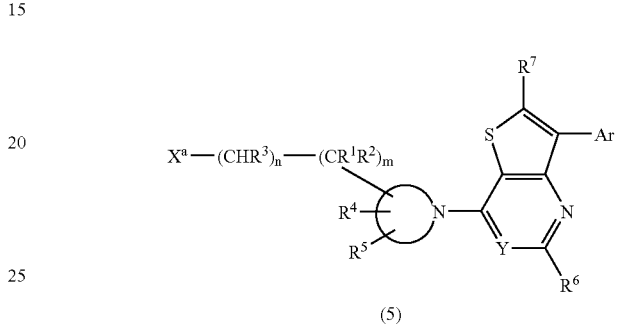

(5)

Step 1:

Compound (3), a compound of the present invention, can be obtained by reacting Compound (1) with Compound (2) in an inert solvent in the presence or absence of a base. Herein, the base includes, for example, amines such as triethylamine, N,N-diisopropylethylamine, pyridine and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

The compound of the present invention can be converted to a salt in an inert solvent with an inorganic acid such as sulfuric acid, hydrochloric acid, hydrobromic acid, phosphoric acid, nitric acid or the like, with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like, with an inorganic base such as lithium hydroxide, sodium hydroxide, potassium hydroxide, calcium hydroxide, magnesium hydroxide, zinc hydroxide, aluminium hydroxide or the like or with an organic base such as ammonia, arginine, lysine, piperazine, choline, diethylamine, 4-phenylcyclohexylamine, 2-aminoethanol, benzathine or the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; esters such as ethyl acetate, ethyl formate and the like; ketones such as acetone, methylethylketone and the like; hydrocarbons such as benzene, toluene and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

Step 2:

The cyano group in compound (4), which was synthesized by the similar method described in step 1, can be converted to the carboxyl group, a $C_{1-5}$alkoxycarbonyl group or the carbamoyl group by using an acid or a base in an inert solvent or without any solvent. An oxidizing agent and/or a crown ether may be used as an additive in this reaction. Herein, the acid includes, for example, organic acids such as formic acid, acetic acid, trifluoroacetic acid, benzenesulfonic acid, methanesulfonic acid, p-toluenesulfonic acid, benzoic acid, trifluoromethanesulfonic acid and the like; inorganic acids such as sulfuric acid, hydrochloric acid, hydrobromic acid, phosphoric acid, polyphosphoric acid, nitric acid, boron trifluoride or the like. The base includes, for example, inorganic bases such as sodium carbonate, potassium carbonate, sodium hydrogencarbonate, potassium hydrogencarbonate, sodium hydroxide, potassium hydroxide, lithium hydroxide, barium hydroxide and the like; metal alcoholates such as sodium methoxide, sodium ethoxide, potassium tert-butoxide and the like. The oxidizing agent includes, for example, hydrogen peroxide, oxygen gas, manganese oxide and the like. The crown ether includes, for example, 18-crown-6, 15-crown-5 and the like. The inert solvent includes, for example, alcohols such as methanol, ethanol, isopropyl alcohol, ethylene glycol, tert-butanol and the like; ethers such as diethyl ether, tetrahydrofuran, 1,4-dioxane, 1,2-dimethoxyethane and the like; hydrocarbons such as benzene, toluene, xylene and the like; esters such as ethyl acetate, ethyl formate and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

Reaction Scheme 3

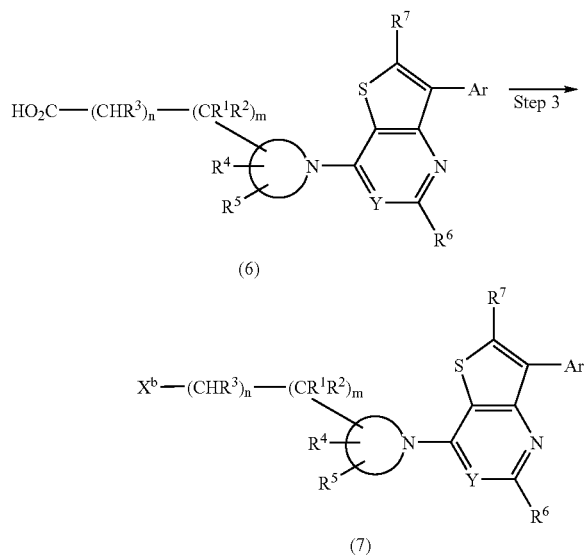

Step 3:

Compound (7), a compound of the present invention, can be synthesized from Compound (6) by conventional methods for amidating a carboxyl group, esterification of a carboxyl group in the presence or absence of an acid or a base or alkylation of a carboxyl group with an alkylating reagent in an inert solvent. Herein, conventional methods for amidating a carboxyl group or esterification of a carboxyl group are: for example, the reaction via a mixed acid anhydride obtained by the reaction of Compound (6) with haloformic acid ester (e.g., ethyl chloroformate or isobutyl chloroformate) or an acid chloride (e.g., benzoyl chloride or pivaloyl chloride); the reaction in the presence of a condensing agent such as N,N'-dicyclohexylcarbodiimide (DCC), 1-(3-dimethylaminopropyl)-3-ethylcarbodiimide hydrochloride (EDCI), carbonyldiimidazole (CDI), diphenylphosphorylazide (DPPA), diethyl cyanophosphate or the like, optionally an additive such as 1-hydroxybenzotriazole (HOBt), N-hydroxysuceinimide, 4-dimethylaminopyridine or the like; or the reaction via an acid halide obtained by the reaction of Compound (6) with a halogenating reagent such as thionyl chloride, oxalyl chloride, or the like. The alkylating reagent is, for example, alkyl halide such as iodomethane, iodoethane, bromomethane, bromoethane and the like. The base includes amines such as triethylamine, N,N-diisopropylethylamine, pyridine, 1,8-diazabicyclo[5.4.0]undec-7-ene, 4-(dimethylamino)pyridine and the like; inorganic bases such as sodium carbonate, potassium carbonate, sodium hydrogencarbonate, potassium hydrogencarbonate and the like. The acid includes, for example, organic acids such as formic acid, acetic acid, trifluoroacetic acid, benzenesulfonic acid, methanesulfonic acid, p-toluenesulfonic acid, benzoic acid, trifluoromethanesulfonic acid and the like; inorganic acids such as sulfuric acid, hydrochloric acid, hydrobromic acid, phosphoric acid, polyphosphoric acid, nitric acid or the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; esters such as ethyl acetate, ethyl formate and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

The compound of the present invention is useful as a therapeutic or prophylactic agent for diseases in which CRF is considered to be involved. For this purpose, the compound of the present invention can be formulated into tablets, pills, capsules, granules, powders, solutions, emulsions, suspensions, injections and the like by a conventional preparation technique by adding conventional fillers, binders, disintegrators, pH-adjusting agents, solvents, etc.

The compound of the present invention can be administered to an adult patient in a dose of 0.1 to 500 mg per day in one portion or several portions orally or parenterally. The dose can be properly increased or decreased depending on the kind of a disease and the age, body weight and symptom of a patient.

EMBODIMENTS OF THE INVENTION

The present invention is concretely explained with reference to the following examples and test example, but is not limited thereto.

EXAMPLE 1

Synthesis of {1-[7-(4-bromo-2,6-dimethyl-phenyl)-2,6-dimethyl-thieno[3,2-d]pyrimidin-4-yl]-piperidin-4-yl}-methanol hydrochloride (compound 1-004)

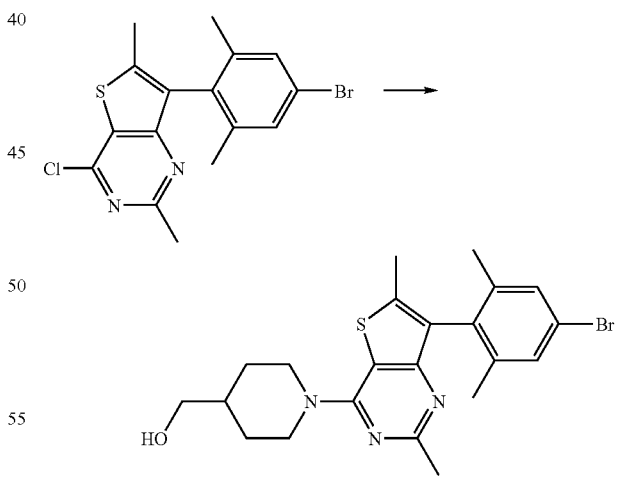

(1) A mixture of 7-(4-bromo-2,6-dimethyl-phenyl)-4-chloro-2,6-dimethyl-thieno[3,2-d]pyrimidine (500 mg), piperidin-4-ylmethanol (226 mg), N,N-diisopropylethylamine (253 mg) in ethanol (1.5 mL) was heated at reflux for 1 day. The reaction mixture was cooled to room temperature, poured into a saturated aqueous sodium hydrogencarbonate, and then extracted with EtOAc. The organic layer washed with brine, dried over anhydrous sodium sulfate and filtered. The filtrate was concentrated under reduced pressure and purified by a silica gel column chromatography (silica gel: Wako Gel (C200), eluent: hexane/EtOAc=3:1) to obtain {1-[7-(4-bromo-2,6-dimethyl-phenyl)-2,6-dimethyl-thieno[3,2-d]pyrimidin-4-yl]-piperidin-4-yl}-methanol as a white solid (568 mg).

(2) To a suspension of {1-[7-(4-bromo-2,6-dimethyl-phenyl)-2,6-dimethyl-thieno[3,2-d]pyrimidin-4-yl]-piperidin-4-yl}-methanol (568 mg) in a mixture (1:1) of EtOH and EtOAc (2 mL) was added 4 M HCl in EtOAc (0.37 mL) under ice-cooling. The mixture was stirred overnight to afford a white crystal. The crystal was collected by filtration to give the title compound (532 mg).

Table 1 lists the compound obtained in Example 1 and compounds obtained by the similar procedure as described in Example 1.

EXAMPLE 2

{1-[7-(4-Bromo-2,6-dimethyl-phenyl)-2,6-dimethyl-thieno[3,2-d]pyrimidin-4-yl]-piperidin-4-yl}-acetic acid

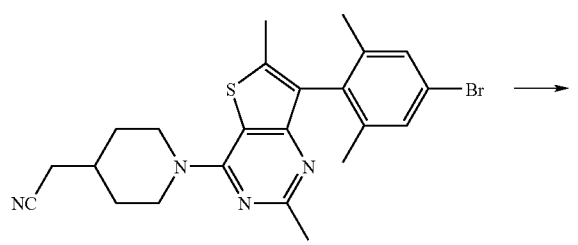

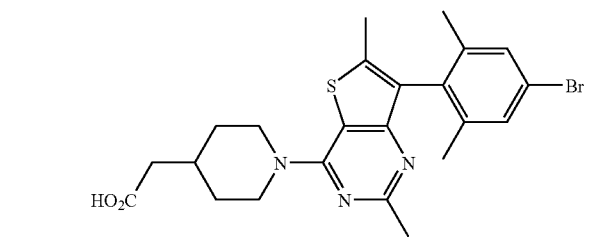

(1) A mixture of {1-[7-(4-bromo-2,6-dimethyl-phenyl)-2,6-dimethyl-thieno[3,2-d]pyrimidin-4-yl]-piperidin-4-yl}-acetonitrile (350 mg) and KOH (492 mg) in a mixture of EtOH (1.5 mL) and $H_2O$ (1.0 mL) in a sealed tube was heated at 105° C. for 3 hours. After concentration of the reaction mixture under reduced pressure, 5% $KHSO_4$ aqueous solution was added and extracted with $CHCl_3$. The organic layer washed with brine, dried over anhydrous $Na_2SO_4$ and concentrated under reduced pressure. The residue was purified by a silica gel column chromatography (silica gel: Wako Gel (C200), eluent: $CHCl_3$/methanol=20:1) to obtain the title compound (164 mg).

Table 1 lists the compound obtained in Example 2 and compounds obtained by the similar procedure as described in Example 2.

EXAMPLE 3

2-{1-[7-(4-Bromo-2,6-dimethyl-phenyl)-2,6-dimethyl-thieno[3,2-d]pyrimidin-4-yl]-piperidin-4-yl}-acetamide

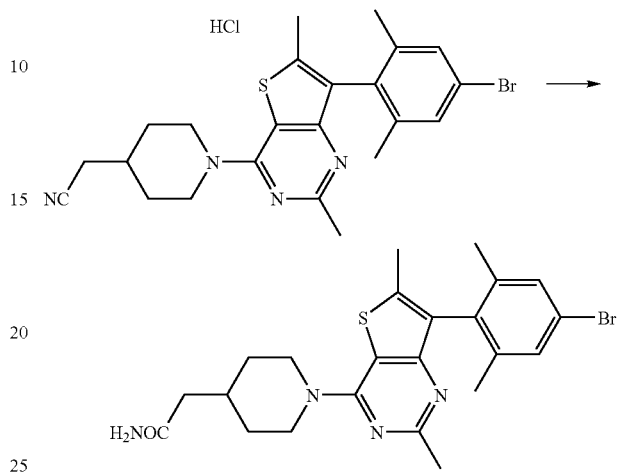

{1-[7-(4-Bromo-2,6-dimethyl-phenyl)-2,6-dimethyl-thieno[3,2-d]pyrimidin-4-yl]-piperidin-4-yl}-acetonitrile hydrochloride (30 mg) was dissolved in c $H_2SO_4$ (0.5 mL) and the solution was stirred at room temperature for 20 hours. After addition of ice, the reaction mixture was made to alkaline (pH 7) with an aqueous NaOH solution and an aqueous $NaHCO_3$ solution. The mixture was extracted with EtOAc and the organic layer washed with brine, dried over anhydrous $Na_2SO_4$ and concentrated under reduced pressure. The residue was purified by a silica gel column chromatography (silica gel: Wako Gel (C200), eluent: EtOAc) to obtain the title compound (20 mg) as a white crystal.

EXAMPLE 4

{1-[7-(4-Bromo-2,6-dimethyl-phenyl)-2,6-dimethyl-thieno[3,2-d]pyrimidin-4-yl]-piperidin-4-yl}-acetic acid ethyl ester

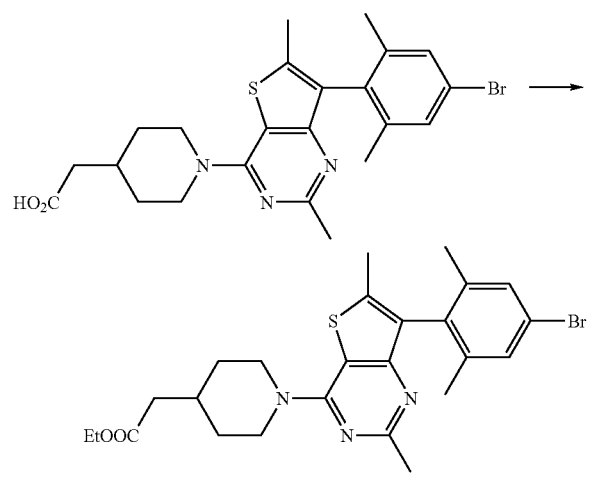

A mixture of {1-[7-(4-bromo-2,6-dimethyl-phenyl)-2,6-dimethyl-thieno[3,2-d]pyrimidin-4-yl]-piperidin-4-yl}-acetic acid (30 mg), iodoethane (97 mg) and $K_2CO_3$ (17 mg) in DMF (1 mL) was stirred at room temperature for 16 hours. To the reaction mixture were added $H_2O$ and EtOAc and separated. The organic layer washed brine, dried over anhydrous $Na_2SO_4$ and concentrated under reduced pressure. The residue was purified by a silica gel column chromatography (silica gel: Wako Gel (C200), eluent: Hexane/EtOAc=4:1) to obtain the title compound (22 mg) as a white crystal.

TABLE 1[*1]

| Com. No. | Ex. No. | [piperidine substructure] | Y | $R^6$ | $R^7$ | —Ar | melting point (°C.) (solvent for crystallization) |
|---|---|---|---|---|---|---|---|
| 1-001 | 1 | 3-(hydroxymethyl)piperidin-1-yl | N | $CH_3$ | H | 2,4-dichlorophenyl | amorphous |
| 1-002 | 1 | 4-(hydroxymethyl)piperidin-1-yl | N | $CH_3$ | H | 2,4-dichlorophenyl | amorphous |
| 1-003 | 1 | 4-(hydroxymethyl)piperidin-1-yl | N | $CH_3$ | H | 4-bromo-2,6-dimethylphenyl | 177-180[*2] (EtOAc/EtOH) |
| 1-004 | 1 | 4-(hydroxymethyl)piperidin-1-yl | N | $CH_3$ | $CH_3$ | 4-bromo-2,6-dimethylphenyl | 242-244[*2] (EtOAc/EtOH) |
| 1-005 | 1 | 4-(2-hydroxyethyl)piperidin-1-yl | N | $CH_3$ | H | 4-bromo-2,6-dimethylphenyl | 192-194[*2] (EtOH) |
| 1-006 | 1 | 4-(2-hydroxyethyl)piperidin-1-yl | N | $CH_3$ | $CH_3$ | 4-bromo-2,6-dimethylphenyl | 192-193[*2] (EtOAc/EtOH) |

TABLE 1*¹-continued
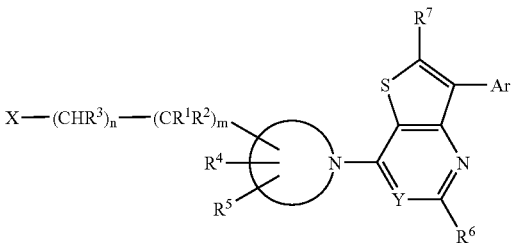
| Com. No. | Ex. No. | (structure) | Y | R⁶ | R⁷ | —Ar | melting point (°C.) (solvent for crystallization) |
|---|---|---|---|---|---|---|---|
| 1-007 | 1 | 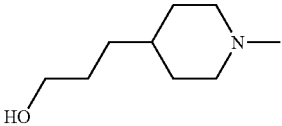 | N | $CH_3$ | H | 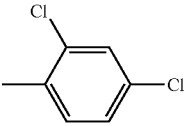 | amorphous |
| 1-008 | 1 | 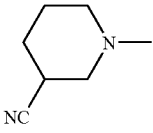 | N | $CH_3$ | H | 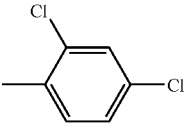 | amorphous |
| 1-009 | 1 | 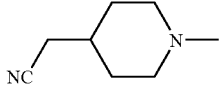 | N | $CH_3$ | H | 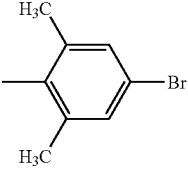 | 163-165*² (EtOAc/EtOH) |
| 1-010 | 1 | 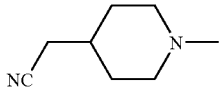 | N | $CH_3$ | $CH_3$ | 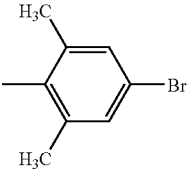 | 202-204*² (EtOAc/EtOH) |
| 1-011 | 1 | 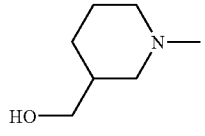 | CH | $CH_3$ | H | 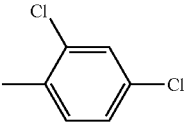 | amorphous |
| 1-012 | 1 | 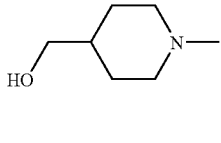 | CH | $CH_3$ | H | 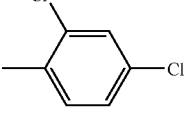 | amorphous |
| 1-013 | 1 | 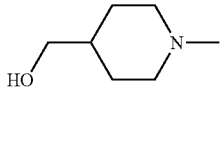 | CH | $CH_3$ | H | 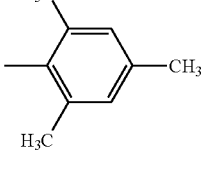 | amorphous |

TABLE 1*1-continued
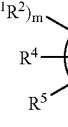
| Com. No. | Ex. No. | X—(CR²R³)ₙ—(CHR¹)ₘ—⟨R⁴,R⁵⟩N— | Y | R⁶ | R⁷ | —Ar | melting point (° C.) (solvent for crystallization) |
|---|---|---|---|---|---|---|---|
| 1-014 | 1 | 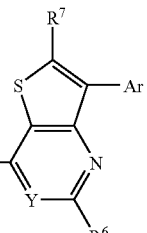 | CH | CH₃ | H | 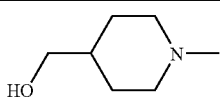 | 228-230*² (EtOAc/EtOH) |
| 1-015 | 1 | 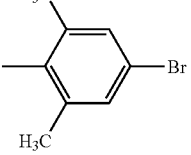 | CH | CH₃ | CH₃ | 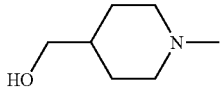 | 234-236*² (EtOAc/EtOH) |
| 1-016 | 1 | 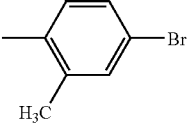 | CH | CH₃ | H | 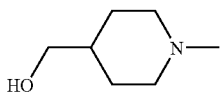 | 196-199*² (EtOAc/EtOH) |
| 1-017 | 1 | 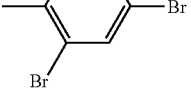 | CH | CH₃ | H | 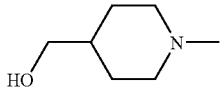 | 231-233*² (EtOAc/EtOH) |
| 1-018 | 1 | 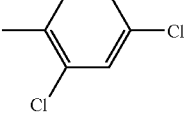 | CH | CH₃ | H | 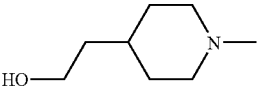 | 172-174*² (EtOAc) |
| 1-019 | 1 | 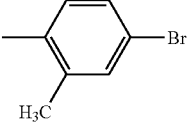 | CH | CH₃ | CH₃ | 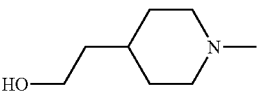 | 182-184*² (EtOAc/EtOH) |
| 1-020 | 1 | 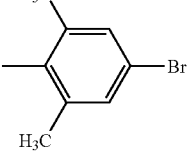 | CH | CH₃ | H | 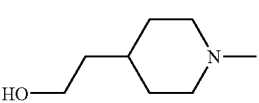 | 166-168*² (EtOAc/EtOH) |

TABLE 1*¹-continued
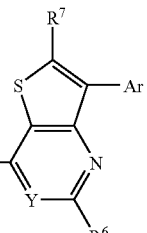
| Com. No. | Ex. No. | (structure with X—(CR²R³)ₙ—(CHR¹)ₘ—[ring with R⁴, R⁵]—N—) | Y | R⁶ | R⁷ | —Ar | melting point (° C.) (solvent for crystallization) |
|---|---|---|---|---|---|---|---|
| 1-021 | 1 | 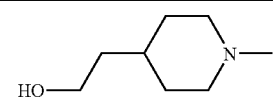 | CH | CH₃ | H | 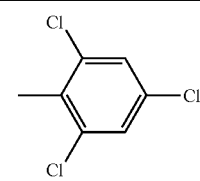 | 158-160*² (EtOAc/EtOH) |
| 1-022 | 1 | 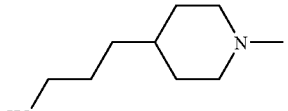 | CH | CH₃ | H | 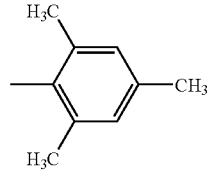 | amorphous |
| 1-023 | 1 | 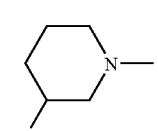 | CH | CH₃ | H | 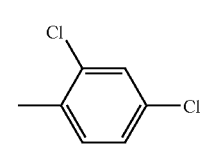 | amorphous |
| 1-024 | 1 | 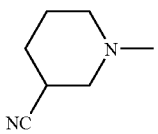 | CH | CH₃ | H | 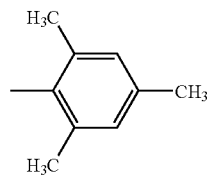 | amorphous |
| 1-025 | 1 | 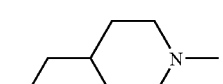 | CH | CH₃ | H | 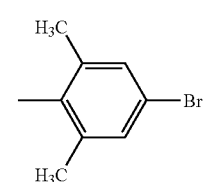 | 186-188*² (EtOAc/IPE) |
| 1-026 | 1 | 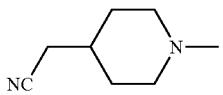 | CH | CH₃ | CH₃ | 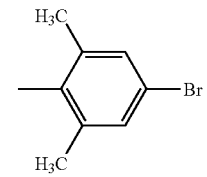 | 135-137*² (EtOAc/EtOH) |
| 1-027 | 1 | 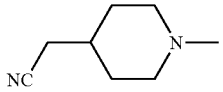 | CH | CH₃ | H | 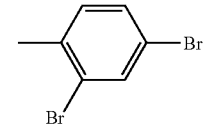 | 179-182*² (EtOAc/EtOH) |

TABLE 1*¹-continued
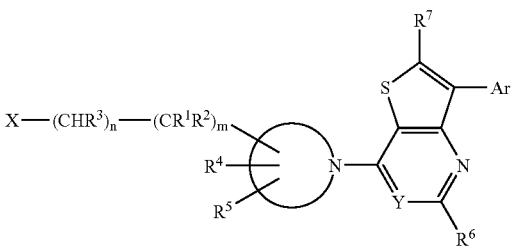
| Com. No. | Ex. No. | <br>R⁵ ──⟨ ⟩── N── <br> R⁴ | Y | R⁶ | R⁷ | —Ar | melting point (° C.) (solvent for crystallization) |
|---|---|---|---|---|---|---|---|
| 1-028 | 1 | 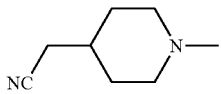 | CH | CH₃ | H | 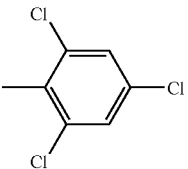 | 203-205*² (EtOAc) |
| 1-029 | 2 | 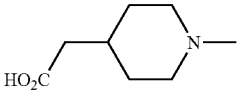 | N | CH₃ | CH₃ | 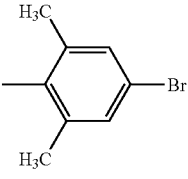 | 268-270 (EtOAc) |
| 1-030 | 2 | 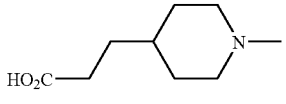 | N | CH₃ | CH₃ | 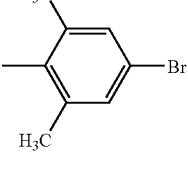 | 222-224 (EtOAc) |
| 1-031 | 3 | 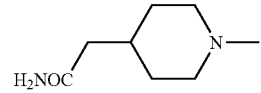 | N | CH₃ | CH₃ | 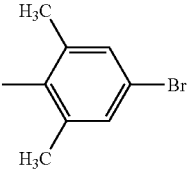 | 212-124*³ |
| 1-032 | 4 | 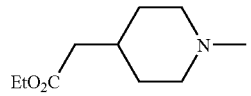 | N | CH₃ | CH₃ | 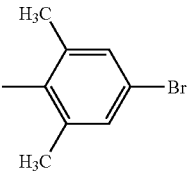 | 110-112*³ |
*¹Com. No. = compound number, Ex. No. = example number, solvent for crystallization; EtOAc = ethyl acetate, EtOH = ethanol, IPE = diisopropylether, Et = ethyl Analytical data of non-crystal compounds are described below.

1-001:
MS (Pos, ES): 408 (M+1)$^+$, 410 (M+3)$^+$, 430 (M+Na)$^+$, 432 (M+Na+2)$^+$; NMR (300 MHz, CDCl$_3$) δ 1.50-2.13 (5H, m), 2.56 (3H, s), 3.48-3.62 (2H, m), 3.71-4.00 (3H, m), 4.06-4.29 (2H, m), 7.35 (1H, dd, J=2.0, 8.4 Hz), 7.52 (1H, d, J=2.0 Hz), 7.57 (1H, d, J=8.4 Hz), 7.84 (1 H, s)

1-002:
MS (Pos, ES): 408 (M+1)$^+$, 410 (M+3)$^+$; HPLC Retention time: 9.69 (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 10 min., to 100% B in 1 min, 100% B for 3 min. and reequilibrate with 100% A for 2.5 min)

1-007:
MS (Pos, ES): 436 (M+1)$^+$, 438 (M+3)$^+$; HPLC Retention time: 9.97 (Xterra MS C18 (Waters, Milford, Mass.) 3.5 μm, 4.6×100 mm); Flow rate 1.6 m/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 10 min., to 100% B in 1 min, 100% B for 3 min. and reequilibrate with 100% A for 2.5 min)

1-008:
MS (Pos, ES): 403 (M+1)$^+$, 405 (M+3)$^+$; HPLC Retention time: 9.94 (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 10 min., to 100% B in 1 min, 100% B for 3 min. and reequilibrate with 100% A for 2.5 min)

1-011:
MS (Pos, ES): 407 (M+1)$^+$, 409 (M+3)$^+$, 429 (M+Na)$^+$, 431 (M+Na+2)$^+$; NMR (300 MHz, CDCl$_3$) δ 1.20-2.12 (5H, m), 2.57 (3H, s), 2.80-3.06 (2H, m), 3.52-4.00 (5H, m), 6.61 (1H, s), 7.33 (1H, dd, J=2.0, 8.4 Hz), 7.51 (1H, d, J=2.0 Hz), 7.63 (1H, d, J=8.4 Hz), 7.73 (1H, s)

1-012:
MS (Pos, ES): 407 (M+1)$^+$, 409 (M+3)$^+$; HPLC Retention time: 10.02 (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 10 min., to 100% B in 1 min, 100% B for 3 min. and reequilibrate with 100% A for 2.5 min)

1-013:
MS (Pos, ES): 381 (M+1)$^+$; HPLC Retention time: 9.22 (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 10 min., to 100% B in 1 min, 100% B for 3 min. and reequilibrate with 100% A for 2.5 min)

1-022:
MS (Pos, ES): 409 (M+1)$^+$; HPLC Retention time: 9.89 (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 10 min., to 100% B in 1 min, 100% B for 3 min. and reequilibrate with 100% A for 2.5 min)

1-023:
MS (Pos, ES): 402 (M+1)$^+$, 404 (M+3)$^+$; HPLC Retention time: 6.40 (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 10 min., to 100% B in 1 min, 100% B for 3 min. and reequilibrate with 100% A for 2.5 min).

1-024:
MS (Pos, ES): 376 (M+1)$^+$; HPLC Retention time: 6.21 (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 10 min., to 100% B in 1 min, 100% B for 3 min. and reequilibrate with 100% A for 2.5 min)

*2: HCl salt

*3: Crystallized on standing from the compound purified (silica gel column chromatography) and dried.

TEST EXAMPLE

CRF Receptor Binding Test

Monkey amygdala membranes were used as a receptor preparation.

$^{125}$I-CRF was used as $^{125}$I-labeled ligand.

Binding reaction using the $^{125}$I-labeled ligand was carried out by the following method described in The Journal of Neuroscience, 7, 88 (1987).

Preparation of Receptor Membranes:

Monkey amygdala was homogenized in 50 mM Tris-HCl buffer (pH 7.0) containing 10 mM MgCl$_2$, 2 mM EDTA and centrifuged at 48,000×g for 20 min, and the precipitate washed once with Tris-HCl buffer. The washed precipitate was suspended in 50 mM Tris-HCl buffer (pH 7.0) containing 10 mM MgCl$_2$, 2 mM EDTA, 0.1% bovine serum albumin and 100 kallikrein units/ml aprotinin, to obtain a membrane preparation.

CRF Receptor Binding Test:

The membrane preparation (0.3 mg protein/ml), $^{125}$I-CRF (0.2 nM) and a test drug were reacted at 25° C. for 2 hours. After completion of the reaction, the reaction mixture was filtered by suction through a glass filter (GF/C) treated with 0.3% polyethylene imine, and the glass filter washed three times with phosphate-buffered saline containing 0.01% Triton X-100. After the washing, the radioactivity of the filter paper was measured in a gamma counter.

The amount of $^{125}$I-CRF bound when the reaction was carried out in the presence of 1 μM CRF was taken as the degree of nonspecific binding of $^{125}$I-CRF, and the difference between the total degree of $^{125}$I-CRF binding and the degree of nonspecific $^{125}$I-CRF binding was taken as the degree of specific $^{125}$I-CRF binding. An inhibition curve was obtained by reacting a definite concentration (0.2 nM) of $^{125}$I-CRF with various concentrations of each test drug under the conditions described above. A concentration of the test drug at which binding of $^{125}$I-CRF is inhibited by 50% (IC$_{50}$) was determined from the inhibition curve.

As a result, it was found that compounds 1-003, 1-004, 1-006, 1-010, 1-012, 1-013, 1-014, 1-015, 1-016, 1-017, 1-018, 1-019, 1-020, 1-021, 1-024, 1-025, 1-026, 1-027 and 1-028 can be exemplified as typical compounds having an IC$_{50}$ value of 100 nM or less.

EFFECT OF THE INVENTION

According to the present invention, compounds having a high affinity for CRF receptors have been provided. These compounds are effective against diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, dermatitides, schizophrenia, pain, etc.

The invention claimed is:
1. A thienopyrimidine compound substituted with a cyclic amino group represented by the following formula [I]:

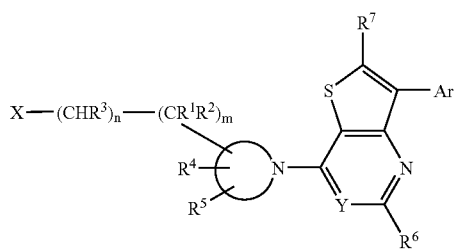

wherein the cyclic amino group is represented by the following formula [II]:

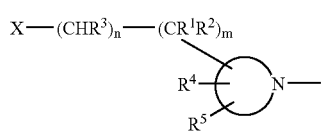

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$alkylene between any different two carbon atoms of the cyclic amine, which cyclic amine is substituted with a group represented by —(CR$^1$R$^2$)$_m$—(CHR$^3$)$_n$—X, R$^4$ and R$^5$ independently on the same or different carbon atoms of the cyclic amine;

X is cyano or hydroxy;
Y is N;

R$^1$ is hydrogen, hydroxy, $C_{1-5}$alkyl, $C_{1-5}$alkoxy-$C_{1-5}$alkyl or hydroxy-$C_{1-5}$alkyl;
R$^2$ is hydrogen or $C_{1-5}$alkyl;
R$^3$ is hydrogen, cyano, $C_{1-5}$alkyl, $C_{1-5}$alkoxy-$C_{1-5}$alkyl or hydroxy-$C_{1-5}$alkyl;
m is an integer selected from 0, 1, 2, 3, 4 and 5;
n is 0 or 1;
R$^4$ is hydrogen, hydroxy, hydroxy-$C_{1-5}$alkyl, cyano, cyano-$C_{1-5}$alkyl or $C_{1-5}$alkyl;
R$^5$ is hydrogen or $C_{1-5}$alkyl;
R$^6$ is hydrogen, $C_{1-5}$ alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, halogen, $C_{1-5}$alkylthio or —N(R$^{12}$)R$^{13}$;
R$^7$ is hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —N(R$^{14}$)R$^{15}$, —CO$_2$R$^{16}$, —CON(R$^{17}$)R$^{18}$, cyano, nitro, $C_{1-5}$alkylthio, trifluoromethyl or trifluoromethoxy;
Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —CO$_2$R$^{19}$, —C(=O)R$^{20}$, —CONR$^{21}$R$^{22}$, —OC(=O)R$^{23}$, —NR$^{24}$CO$_2$R$^{25}$, —S(=)$_r$NR$^{26}$R$^{27}$, trifluoromethyl, trifluoromethoxy, difluoromethoxy, fluoromethoxy, methylenedioxy, ethylenedioxy and —N(R$^{28}$)R$^{29}$;
R$^{12}$, R$^{13}$, R$^{14}$ and R$^{15}$ are the same or different, and independently are hydrogen or $C_{1-5}$alkyl;
R$^{16}$, R$^{19}$ and R$^{25}$ are the same or different, and independently are hydrogen or $C_{1-5}$alkyl, $C_{3-8}$cycloalkyl, $C_{3-8}$cycloalkyl-$C_{1-5}$alkyl, aryl or aryl-$C_{1-5}$alkyl;
R$^{17}$, R$^{18}$, R$^{20}$, R$^{21}$, R$^{22}$, R$^{23}$, R$^{24}$, R$^{26}$, R$^{27}$, R$^{28}$ and R$^{29}$ are the same or different, and independently are hydrogen, $C_{1-5}$alkyl or $C_{3-8}$cycloalkyl;
r is 1 or 2 or pharmaceutically acceptable salts thereof.

2. The thienopyrimidine compound substituted with the cyclic amino group according to claim 1 represented by formula [III],

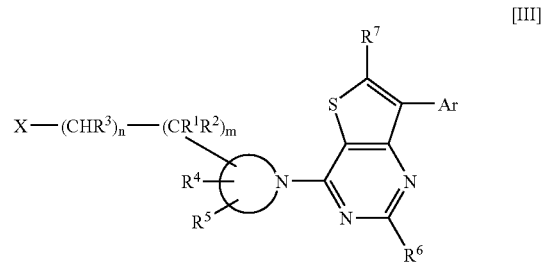

wherein X is cyano; the cyclic amino group is a 4- to 7-membered saturated cyclic amine; n is 0; m is an integer selected from 0, 1, 2 and 3; R$^1$, R$^2$, R$^4$ and R$^5$ are hydrogen; R$^6$ is $C_{1-5}$alkyl; R$^7$ is hydrogen or $C_{1-5}$alkyl; and Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N(R$^{28}$)R$^{29}$ (wherein R$^{28}$ and $R^{29}$ are the same or different, and independently are hydrogen or $C_{1-3}$alkyl), or pharmaceutically acceptable salts thereof.

3. The thienopyrimidine compound substituted with the cyclic amino group according to claim 2 represented by formula [III], wherein X is cyano; the cyclic amino group is a 6-membered saturated cyclic amine; n is 0; m is 0 or 1; $R^1$, $R^2$, $R^4$ and $R^5$ are hydrogen; $R^6$ is $C_{1-5}$alkyl; $R^7$ is hydrogen or $C_{1-5}$alkyl; and Ar is phenyl which phenyl is substituted with two or three substituents, which are the same or different, selected from the group consisting of halogen and $C_{1-3}$alkyl, or pharmaceutically acceptable salts thereof.

4. The thienopyrimidine compound substituted with the cyclic amino group according to claim 1 represented by formula [III],

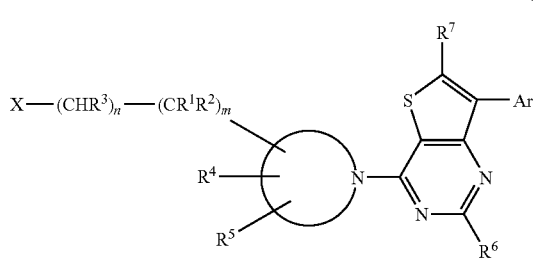

wherein X is hydroxy; the cyclic amino group is a 4- to 7-membered saturated cyclic amine; n is 0; m is an integer selected from 1, 2 and 3; $R^1$, $R^2$, $R^4$ and $R^5$ are hydrogen; $R^6$ is $C_{1-5}$alkyl; $R^7$ is hydrogen or $C_{1-5}$alkyl; and Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N($R^{28}$)$R^{29}$ (wherein $R^{28}$ and $R^{29}$ are the same or different, and independently are hydrogen or $C_{1-3}$alkyl), or pharmaceutically acceptable salts thereof.

5. The thienopyrimidine compound substituted with the cyclic amino group according to claim 1 represented by formula [III],

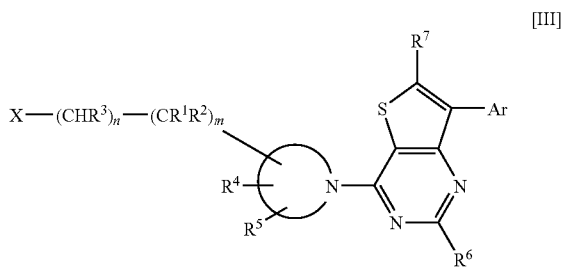

wherein X is hydroxy; the cyclic amino group is a 6-membered saturated cyclic amine; n is 0; m is an integer selected from 1, 2 and 3; $R^1$, $R^2$, $R^4$ and $R^5$ are hydrogen; $R^6$ is $C_{1-5}$alkyl; $R^7$ is hydrogen or $C_{1-5}$alkyl; and Ar is phenyl which phenyl is substituted with two or three substituents, which are the same or different, selected from the group consisting of halogen and $C_{1-3}$alkyl, or pharmaceutically acceptable salts thereof.

6. A compound represented by formula [I] according to claim 1, which is selected from the group consisting of
{1-[7-(4-Bromo-2,6-dimethyl-phenyl)-2-methyl-thieno[3,2-d]pyrimidin-4-yl]-piperidin-4-yl}-methanol,
{1-[7-(4-bromo-2,6-dimethyl-phenyl)-2,6-dimethyl-thieno[3,2-d]pyrimidin-4-yl]-piperidin-4-yl}-methanol,
2-{1-[7-(4-bromo-2,6-dimethyl-phenyl)-2,6-dimethyl-thieno[3,2-d]pyrimidin-4-yl]-piperidin-4-yl}-ethanol, and
{1-[7-(4-bromo-2,6-dimethyl-phenyl)-2,6-dimethyl-thieno[3,2-d]pyrimidin-4-yl]-piperidin-4-yl}-acetonitrile.

7. A composition comprising a thienopyrimidine compound substituted with a cyclic amino group, or a pharmaceutically acceptable salt thereof according to claim 1, as an active ingredient and a pharmaceutically acceptable carrier.

* * * * *